United States Patent [19]

Wu

[11] Patent Number: 5,188,607
[45] Date of Patent: Feb. 23, 1993

[54] VALVE CATHETER CONNECTOR ASSEMBLY

[76] Inventor: Thomas Wu, 74 Huntersfield Rd., Delmar, N.Y. 12054

[21] Appl. No.: 791,482

[22] Filed: Nov. 12, 1991

[51] Int. Cl.$^5$ .............................................. A61M 5/00
[52] U.S. Cl. ................... 604/167; 604/169; 604/256
[58] Field of Search ..................... 604/167, 169, 256

[56] References Cited

U.S. PATENT DOCUMENTS

| | | | |
|---|---|---|---|
| 3,565,078 | 2/1971 | Valliancourt | 128/349 |
| 4,449,693 | 5/1984 | Gereg | 251/149.8 |
| 4,475,548 | 10/1984 | Muto | 604/167 |
| 4,559,043 | 12/1985 | Whitehouse et al. | 604/201 |
| 4,576,595 | 3/1986 | Aas | 604/256 |
| 4,628,928 | 12/1986 | Lowell | 604/167 |
| 4,673,400 | 6/1987 | Martin | 604/283 |
| 4,769,017 | 9/1988 | Faith et al. | 604/283 |
| 4,781,703 | 11/1988 | Walker et al. | 604/264 |
| 4,842,591 | 6/1989 | Luther | 604/283 |
| 4,850,953 | 7/1989 | Haber | 604/256 |
| 4,886,501 | 12/1989 | Johnston et al. | 604/175 |
| 4,966,588 | 10/1990 | Rayman et al. | 604/165 |
| 5,061,253 | 10/1991 | Yoshida | 604/256 |
| 5,064,416 | 11/1991 | Newgard et al. | 604/167 |
| 5,080,654 | 1/1992 | Picha et al. | 604/167 |

Primary Examiner—Paul J. Hirsch
Attorney, Agent, or Firm—Schmeiser, Morelle & Watts

[57] ABSTRACT

In a catheter connector assembly the catheter tube is secured within a resilient sleeve valve. The sleeve valve acts as the hub of the catheter connector for reception of male connector tube while simultaneously sealing the catheter tube against retrograde blood flow until the male connector is fully inserted.

4 Claims, 2 Drawing Sheets

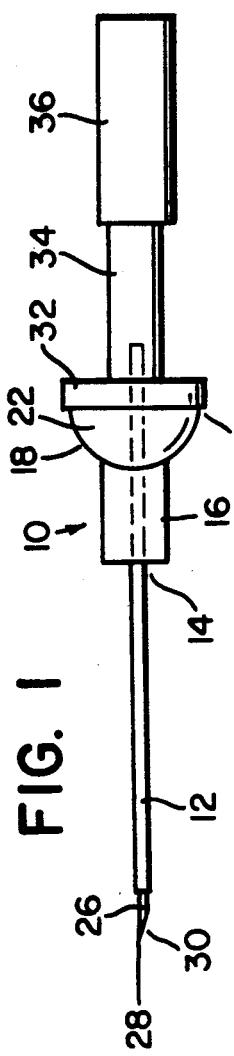
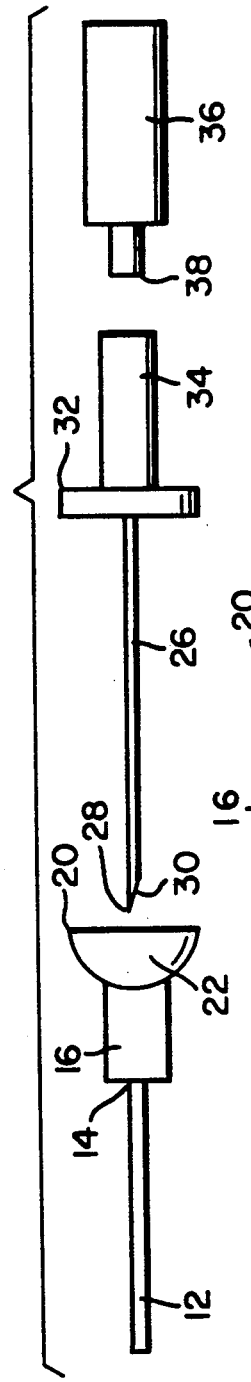
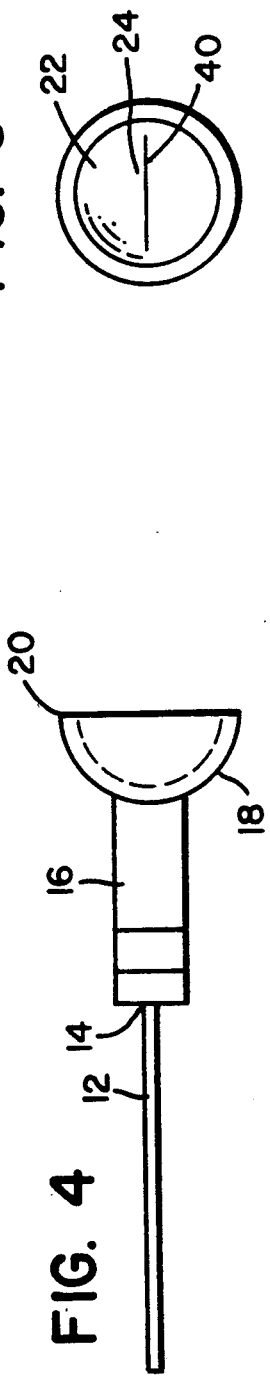
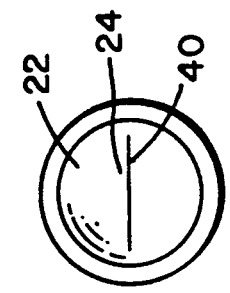
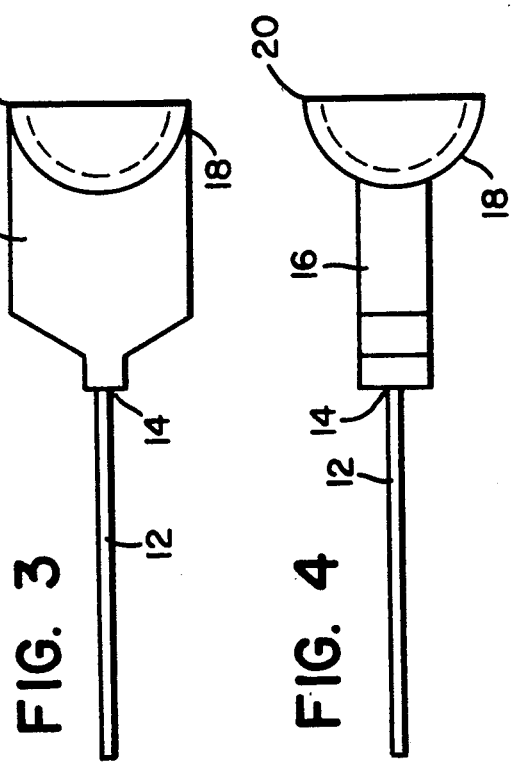

VALVE CATHETER CONNECTOR ASSEMBLY

FIELD OF THE INVENTION

Generally this invention relates to the field of catheters which utilize inner needles for vascular access. More specifically, this invention lies in the field of catheter connectors which utilize valve mechanisms to prevent retrograde blood flow after the needle is withdrawn from the catheter and before the desired tube is secured within the catheter connector.

BACKGROUND OF THE INVENTION

Intravascular catheters are widely used in the medical field as they provide advantages over the various types of needles which were previously used. In particular, where medical treatment requires either continuous or else quick and easy access to an intravascular site the use of a catheter is often the preferred mode of treatment.

While catheters provide many advantages for vascular access, one significant problem remains. The primary problem with catheters is the fact that the removal of the inner needle creates an open passageway for the retrograde flow of blood out through the catheter and its hub.

The procedure for removing the needle from the catheter requires the physician, or other health personnel, to withdraw the needle with one hand while the other hand stabilizes and/or further inserts the catheter in the vessel, usually by holding the hub. Thus, the physician must withdraw the needle, put it down and seize the male connector of the tube, syringe or similar item, which will be secured within the hub of the catheter, and make the connection. Up until the time the connection is made it is common to experience retrograde blood flow out of the catheter. The greatest concern relative to this blood flow is of course the possibility of transmitting diseases such as hepatitis or Acquired Immune Deficiency Syndrome (AIDS) to the attending health personnel. Of a lesser, though still significant degree, is the extremely detrimental effect that seeing this loss of blood has upon the patient. Depending upon the emotional stability of the patient and their experiences in this area the range of emotions can go anywhere from mild annoyance to virtual hysteria which, depending upon the patient's other conditions, could cause a severe reaction. Of a less severe nature is the fact that the blood often stains the patient's clothing, bedding and the like which requires the patient to be moved as these items are changed.

In an attempt to avoid these problems many physicians will attempt to hold the male connector in the same hand which is being used during the withdrawal of the needle to accomplish a quicker insertion of the male adapter into the catheter hub. The practice of this procedure will generally enable the physician to accomplish this transfer with only a small loss of blood due to retrograde flow, however, even a small loss of blood can be dangerous if the blood is contaminated. Specifically, the needle which is withdrawn, and perhaps contaminated, is secured between two fingers, most commonly the ring finger and middle finger, while the sterile connector which is to be inserted into the catheter hub, is held between the thumb and forefinger. As is readily recognizable, minimal control is had over the needle and while attention is being paid to maintaining the connector in a sterile condition and inserting it into the hub, the catheter needle is exposed and being moved which greatly increases the possibility of sticking either the physician or perhaps an attendant nurse who could be restraining the patient or otherwise required to be in close proximity to the treatment site.

Some physicians will remove the needle from the catheter and quickly place it at bed side, or hand it to an attending nurse for disposal, before trying to secure the connector in place. While this method may be preferable to the single handed method discussed above, whatever methods are employed there is always the danger of needle injury while one is connecting the male connector to the catheter.

Clearly, the safest approach is to remove the needle from the catheter and then dispose of it before uncovering the sterile tip of the connector and inserting it into the catheter hub. Such an approach however, is of course not possible unless there is a valve mechanism which will prevent the retrograde flow of blood. To accomplish this, a valve mechanism accommodating both the inner needle and the male connector is required. To fabricate such a valve two important criteria must be considered.

First, size requirements of a catheter make it difficult to fabricate a proper valve mechanism. For example, a valve mechanism would normally be placed within the plastic hub of the catheter the size of which is determined by connectors which are inserted therein. Since the hub is a rather small opening, the valve mechanism is limited in size.

Second, the valve must accommodate an inner needle which is passed through the hub and catheter with the distal end of the needle extending out of the catheter end for insertion into a blood vessel. Then, after the inner needle is removed, the valve must easily accommodate the insertion of a male connector.

Presently available valves, such as cylindrical shaped plugs, ball-ring valves, collapsible tube segment, diaphragm etc. do not meet the above two requirements. Presently only a septum valve could be considered as meeting these requirements. However, the use of a septum as a valve causes other problems.

First, if the septum is not thick enough, upon withdrawal of the needle, the bevel of the needle which is at the distal end, will span the distance from one side of the septum to the other, thus providing an outlet for retrograde blood flow. Furthermore, the septum must be located in the hub in such a way that it can be secured in place. However, securing the septum within the hub by a hinged connection causes a dead space between the septum and the proximal end of the catheter tubing. Upon injection, air caught in the dead space is injected into the person's blood stream which may cause an air embolism depending upon the amount of air and the injection site. Even when the injected air is not dangerous it is discomforting to the patient. Also, whenever a needle is required to pierce a substance, there is the possibility that part of the septum could be cut off and lodged in the bore of the needle. This is especially true if the needle has to be put through the septum more than once as may be the case if the needle is not aligned exactly enough to slide into the catheter tubing.

Compounded with the above difficulties is the fact that after the needle is removed, the valve mechanism must be movable to an open position upon insertion of the male connector from the tube or other device which is to be secured within the hub of the catheter. Since these male connectors are not designed to pierce the septum, the septum must be moved out of the way by some other mechanism.

Thus, these septum valves are generally 2-way, hinged along one side so they open upon insertion of the male connector. Therefor these septums require an additional device such as a plug to prevent the septum from opening in an outward direction due to blood pressure. Furthermore, often, while a catheter is in place, tubes must be changed and the constant insertion and withdrawal of the male connector can loosen the valve, if not secured properly within the hub, thus causing leakage around the sides of the septum or in the worst case, complete removal of the septum upon the withdrawal of the male connector.

SUMMARY OF THE INVENTION

The subject invention overcomes the difficulties experienced in the prior art by providing a duel function catheter hub which serves both as a receptacle for a male connector or needle, and as a valve to prevent retrograde blood flow. This is accomplished by manufacturing the hub from a elastic resilient material. Moving proximally from the catheter tube, there is first, a sleeve valve portion. The sleeve valve is of unitary configuration and formed so that there is a passageway between the opposing walls of the sleeve. The passageway is closed when the sleeve valve is in its quiescent state due to the elasticity of the walls. Continuing to move proximally the sleeve expands into a cupule with the closed passageway at the base of the cupule and opening thereinto. Thus, the hub itself is unitary in configuration and forms its own valve system to prevent the retrograde flow of blood after the needle is removed.

The benefits of the subject invention over the prior art can be appreciated when one considers the actual operation of the invention.

First, the needle which needs to be inserted through the catheter does not have to pierce a septum but instead simply separates the sleeve walls as it is advanced through the passageway and into the catheter. The passageway, which is sealed in its quiescent state, forms a noticeable line at the base of the cupule so that the needle can be easily inserted into the passageway without having to pierce any portion of the hub. Generally, the needle will be located in the cupule with the needle extending through the cupule into the passageway and being secured therein by the opposing walls. It is in this configuration that the physician will generally receive the catheter system.

The needle is inserted into the patient as with any catheter system. When the needle is located properly within the blood vessel blood will flow back through the needle and, depending on the system, will generally enter a clear reservoir in the hub of the needle thus alerting the physician to the fact that the needle is properly located. It should be noted that this clear reservoir in the hub of the needle is generally sealed to prevent the spilling of blood.

Once properly located, the physician can secure the catheter by holding the catheter hub in one hand and removing the needle with the other hand. As the needle is removed, the opposing walls of the sleeve valve will come together due to their elasticity forming a seal around the point and bevel of the needle. Since the entire hub forms the valve, there is virtually no dead space in which air can collect. While the needle is being withdrawn and thereafter, the sleeve valve will prevent the retrograde flow of blood so that the physician may remove the needle and, keeping his attention on the needle, dispose of it properly in a medical waste containment receptacle.

The physician may then uncover the sterile male connector from the tubing or other implement which is to be secured to the catheter. Once uncovered, the male connector is inserted into the cupule which, by its form, will direct the male connector to its base and the entrance to the passageway. The connector is inserted, as would normally be done, into the hub but with the improved effect that the male connector is virtually opening the sleeve valve as it presses into and separates the walls thereof. The connector is advanced until it comes to the end of the passageway which is essentially in contact with the proximal end of the catheter tubing. Thus, the connection is made with no loss of blood and with virtually no dead spaces that could cause air to be injected into the patient.

A further and unexpected benefit is the fact that the sleeve valve assures a more positive connection between the male connector and the hub for two primary reasons. First, elasticity of the walls close about the entire male connector. Secondly, because the male connector must be inserted completely in order to fully open the passageway and form a communication between the male connector and the catheter tubing no flow through the male connector will be possible until it is completely inserted and secured in place.

Should it be necessary to exchange male connectors, the walls of the sleeve valve will close as the male connector is withdrawn thus once again sealing the valve against retrograde blood flow. Similarly, when the new male connecter is inserted, it must be properly located completely within the sleeve valve before flow through the male connector can be accomplished.

I have also found that the resilient nature of the hub is beneficial as it easily conforms to the person's body surface and is easily secured in place by tape or the like.

BRIEF DESCRIPTION OF THE DRAWINGS

FIG. 1 is a side elevational view of the catheter system of the subject invention;

FIG. 2 is an exploded view of the various elements of the catheter system;

FIG. 3 is a top view of the catheter tube and hub;

FIG. 4 is a side elevational view of the catheter tube and hub;

FIG. 5 is a rear view showing the inside of the coupule and the entryway to the passage;

DETAILED DESCRIPTION OF THE PREFERRED EMBODIMENTS

Figure 6:
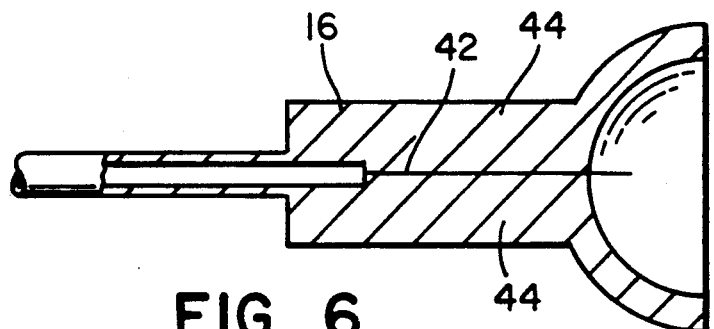
FIG. 6 is a side elevational view with partial breakaway of the valve and catheter.

As shown in FIG. 1, the valve catheter connectors assembly is generally designated as 10. This assembly consists of a catheter tube 12 which at its proximal end 14 is secured to the sleeve valve 16. Continuing proximally, the sleeve valve 16 opens into a cupule 18 having a rim 20, sides 22 and base 24.

Extending through the connector assembly 10 is a needle 26 the most distal end of which has a point 28 and a bevel portion 30 which extends out of the catheter tube 12. In its assembled position, the needle hub 32 abuts the cupule 18 and the needle 26 is secured in the sleeve valve 16.

The needle hub 32 has a reservoir portion 34 behind it which is clear so that when the needle 26 is located within a patient's blood vessel, the blood will flow through the needle and into the reservoir 34 thereby indicating to the physician that the needle is properly located. A cap 36 has a stud portion 38 which is inserted into the reservoir to prevent blood from escaping (see FIG. 2).

FIG. 2 is an exploded view of the assembly 10 shown in FIG. 1 and more clearly discloses the various separate parts. It should be noted that the needle 26 and its associated assembly is one of various configurations which may be used with the connector assembly invention 10. However, since this needle assembly is one of the most commonly used, it is shown here to explain the advantages of the subject invention. In these configurations, it is expected that the catheter tube 12 will be formed unitarily with the sleeve valve 16. Thus, it would be made of the same material or of compatible materials which can form a unitary structure.

FIG. 3 is a top view showing the assembly as it would lay after insertion into the patient. It should be noted that the sleeve valve 16 has a significant width which aids in securing it to the patient by means of tape and also allows for some conforming to the patient's body. As shown in the side view of FIG. 4 the sleeve is thinner in height than width and the external surface of the cupule 18 is rounded.

The view of FIG. 5 shows a slit 40 which is the entrance to passageway 42 as shown in FIG. 6. Because the sleeve is made of a resilient material the passageway 42 is closed while the sleeve is in its quiescent state. Thus, the walls 44 of the sleeve valve 16 press against each other closing the passageway 42 with sufficient force to prevent retrograde blood flow from opening the passageway. The passageway 42 extends completely through the sleeve from the proximal end of the catheter to the base 24 of the cupule 18.

The slit 40 is centrally located at the base of the cupule 18. In this manner the sides 22 of the cupule 18 serve as a guide directing the male connector to the entrance or passageway 42. Due to the resilience of the sleeve valve 16 the walls 44 will virtually close around the tip of the male connector. Thus, there is no retrograde blood flow as the male connector is drawn out of the passageway. Furthermore, there is virtually no dead space between the male connector and the proximal end 14 of the catheter tube 12.

Figure 8:
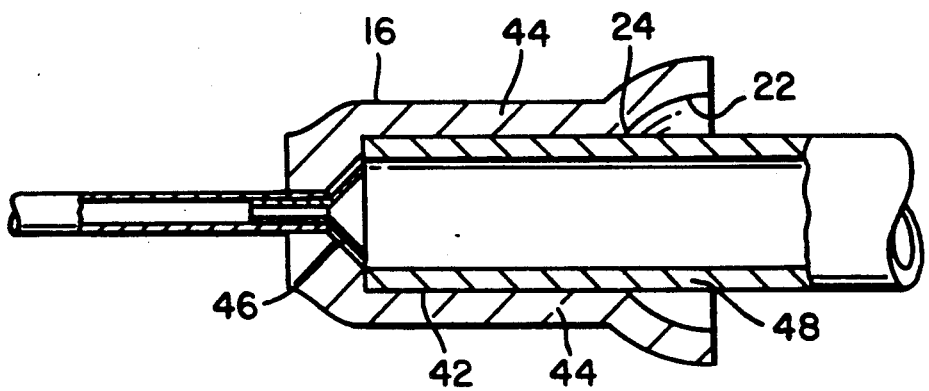
FIG. 8 is a side elevational view and partial breakaway of an alternate embodiment securing the catheter tubing in place within the valve and also showing the insertion of a male connector.

FIG. 8 shows an alternate embodiment wherein the proximal end 14 of the catheter tube 12 has a base portion 46 which acts as a guide for further centering the inner needle 26. In this alternate embodiment the base portion 46 may be made of a piece of metal which is secured within the catheter tube 12 and secured within the distal end of the sleeve valve 16. In such a configuration the catheter tube 12 would most likely be made of a plastic material while the sleeve valve would be of a rubber or similar fabrication. Nevertheless, as stated heretofore it is possible to use other materials such as silicone or the like which are acceptable to the body yet provide sufficient resilience to form the sleeve valve as required. In such an arrangement the entire catheter connector assembly 10 could be fabricated in a mold.

Figure 7:
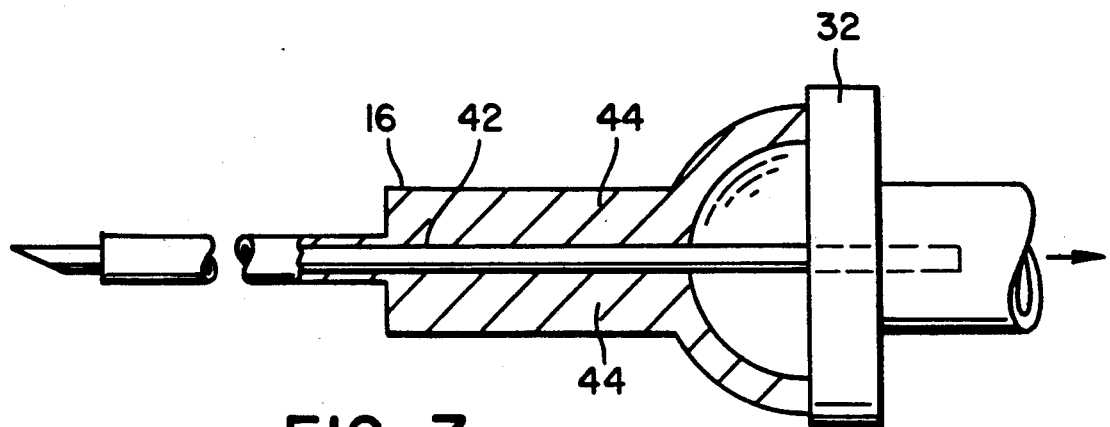
FIG. 7 is a side elevational view and partial breakaway showing the location of the needle within the valve and catheter tubing.

In operation, the physician takes the valve catheter connector assembly 10 which is essentially shown in FIG. 1 wherein the needle 26 protrudes out of the distal end of the catheter tube 12. The needle is inserted into the patient's blood vessel after which the needle 26 is withdrawn. As shown in FIG. 7 the resilient walls 44 of the sleeve valve 16 close around the needle 26. Similarly, once the needle 26 is within the sleeve valve 16 the walls 44 will seal the space between the catheter tube 12 and the needle and also block any flow into the needle bevel 30.

Once the needle is removed the connector assembly 10 appears substantially as shown in cross section in FIG. 6 wherein the passageway 42 is sealed and the physician can appropriately discard of the needle 26. Thereafter a male connector 48 (as shown in FIG. 8) is inserted into the sleeve valve 16. More specifically, the male connector first enters the coupule 18, wherein sides 22 act as a guide directing the male connector 48 to the base 24 and into the centrally located slit 40. The connector is then inserted through the sleeve valve 16 to the proximal end 14 of the catheter tube 12. Due to the fact that the passageway 42 is sealed no flow is possible through the male connector 48 until it is inserted fully within the sleeve valve 16 and connects with the proximal end 14. Changing of the male connector which may be a portion of a tube, syringe or the like will function in the same manner so that retrograde blood flow is prevented and there is no communication between the catheter tube 12 and the exterior of the connector assembly until a new male connector is fully inserted within the sleeve.

While the above describes the preferred embodiment of the invention it should be appreciated that many variations may be made without departing from the essence of the invention, the scope of which is defined by the appended claims.

What is claimed is:

1. A valve catheter connector assembly system for preventing blood pooling and retrograde blood flow comprising:

a catheter adapted to receive a needle therethrough, said catheter having a distal end from which said needle may extend, the proximal end of said catheter mating with a valve system further comprising;

a base portion from which the catheter protrudes;

a sleeve valve extending from said base portion, the entire sleeve valve being made of resilient material, said sleeve valve having opposing walls which form a passageway through said sleeve which extends from the proximal end of the catheter through the length of said sleeve, said opposing walls pressing against each other along substantially their entire length to compress and seal said passageway when said sleeve valve is in its quiescent state such that said passageway is completely closed along its length thereby virtually eliminating any dead space within the sleeve valve, said passageway opening along its length forming a direct unobstructed passageway through the sleeve to the proximal end of the catheter upon insertion of a male connector, the proximal end of the valve system adapted to receive the male connector into the passageway, whereby said passageway is opened along its entire length only by the complete insertion of said male connector to a point substantially adjacent to the proximal end of the catheter.

2. The invention of claim 1 wherein the proximal end of the catheter is unitary with the base portion of the valve system, said entire catheter connector assembly system being molded as a single unitary piece.

3. The invention of claim 1 wherein the proximal end of said catheter has a guide for the insertion of said needle.

4. The invention of claim 1 wherein the proximal end of the valve system is formed in a cupulate shape, and the passageway is substantially centrally located at the base of the cupule, whereby the inside of said cupule acts as a guide directing the male connector into the passageway.

* * * * *